(12) United States Patent
Hensman et al.

(10) Patent No.: US 7,834,196 B2
(45) Date of Patent: Nov. 16, 2010

(54) PROCESS FOR THE PREPARATION OF N-ALKYL-PYRROLIDONES

(75) Inventors: John Richard Hensman, London (GB); Riyaz Ezzuddin Khambati, London (GB)

(73) Assignee: Davy Process Technology Limited, London (GB)

( * ) Notice: Subject to any disclaimer, the term of this patent is extended or adjusted under 35 U.S.C. 154(b) by 756 days.

(21) Appl. No.: 11/570,179

(22) PCT Filed: Jun. 1, 2005

(86) PCT No.: PCT/GB2005/002170

§ 371 (c)(1), (2), (4) Date: Jun. 22, 2007

(87) PCT Pub. No.: WO2005/121083

PCT Pub. Date: Dec. 22, 2005

(65) Prior Publication Data

US 2007/0270596 A1    Nov. 22, 2007

(30) Foreign Application Priority Data

Jun. 9, 2004    (GB) ................................. 0412875.7

(51) Int. Cl.
   *C07D 207/12*    (2006.01)
   *C07D 307/20*    (2006.01)
(52) U.S. Cl. ...................................... 548/543; 549/313
(58) Field of Classification Search ................. 548/543; 549/313
   See application file for complete search history.

(56) References Cited

U.S. PATENT DOCUMENTS

| 2,964,535 A | 12/1960 | Clements |
| 7,227,029 B2 * | 6/2007 | Rudloff et al. .............. 548/543 |

FOREIGN PATENT DOCUMENTS

| JP | 06228088 | 8/1994 |
| JP | 2000256312 | 9/2000 |
| JP | 2001002640 | 1/2001 |
| JP | 2001354646 | 12/2001 |
| JP | 2001354647 | 12/2001 |
| WO | 9952867 A1 | 10/1999 |
| WO | 03053924 A1 | 7/2003 |

OTHER PUBLICATIONS

International Preliminary Report on Patentability for PCT/GB2005/002170, dated Dec. 28, 2006.
International Search Report and Written Opinion for PCT/GB2005/002170, dated Aug. 23, 2005.

* cited by examiner

*Primary Examiner*—Robert Havlin
(74) *Attorney, Agent, or Firm*—Senniger Powers LLP

(57) ABSTRACT

A process for the production of N-alkylpyrrolidone from γ-butyrolactone and monoalkylamine in the liquid phase comprising the steps of: feeding monoalkylamine and γ-butyrolactone, in the absence of water or in the presence of less than about 1 wt % of water, to a reaction zone to form a reaction mixture; heating the reaction mixture; withdrawing a product stream from the reaction zone and passing the stream to a distillation zone comprising at least one distillation column operated at sub-atmospheric pressure; adding water to the distillation zone; isolating at least one overhead stream from the distillation zone comprising monoalkylamine, water and optionally N-alkyl-pyrrolidone and condensing the overhead stream against cooling water.

10 Claims, 1 Drawing Sheet

PROCESS FOR THE PREPARATION OF N-ALKYL-PYRROLIDONES

CROSS-REFERENCE TO RELATED APPLICATIONS

Figure 1:
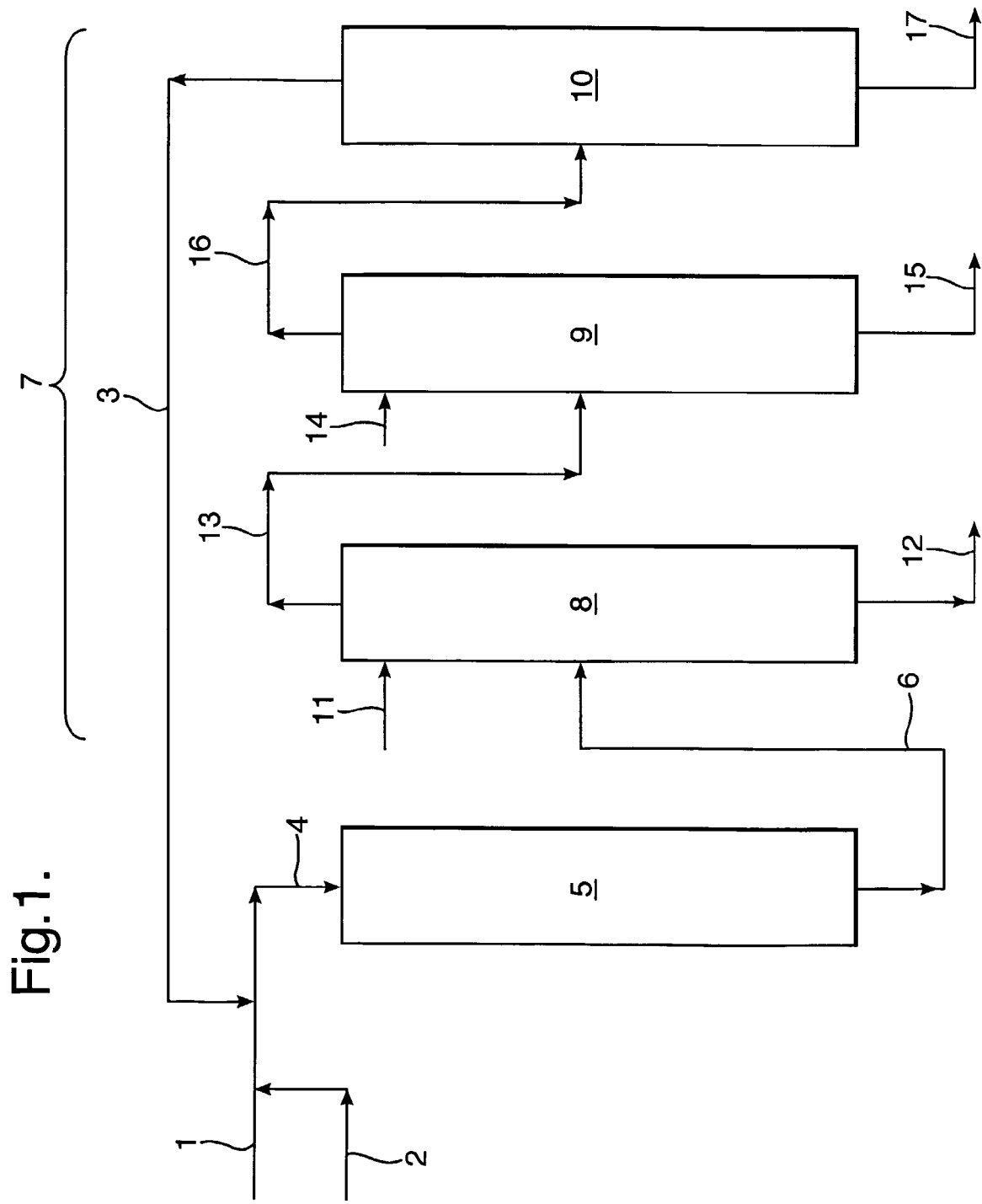

This application is based on and claims the benefit of International (PCT) Application Serial No. PCT/GB2005/002170, filed Jun. 1, 2005, which claims priority from GB 0412875.7, filed Jun. 9, 2004, both of which are herein incorporated by reference in their entirety.

The present invention relates to a process for the production of N-alkyl-pyrrolidones. More preferably it relates to the production of N-methyl-pyrrolidone. Most preferably it relates to a process for the production of N-methyl-pyrrolidone by the reaction of γ-butyrolactone with monomethylamine in the liquid phase in the absence of a catalyst.

N-methyl-pyrrolidone and other pyrrolidones are conventionally produced from γ-butyrolactone and the appropriate alkylamine. The γ-butyrolactone may be produced by the hydrogenation of maleic esters in the vapour phase. The maleic esters are produced from maleic anhydride which in turn is generally produced from the oxidation of butane. In view of the large number of process steps present, the process costs are high and since N-methyl-pyrrolidone and other pyrrolidones are commercially important commodity chemicals particularly as solvents or reaction mediums it is desirable to provide a process which provides a cost-effective route to the pyrrolidones.

Ullmann's Encyclopedia of Industrial Chemistry, 5th Ed., Vol A22 pages 458 to 459 explains that large-scale production of N-methyl-pyrrolidone is achieved through the conversion of γ-butyrolactone with monomethylamine in a shaft reactor at a temperature of from about 200° C. to about 350° C. and at a pressure of about 10 MPa.

A process for the production of N-methyl-pyrrolidone is described in WO 03/053924. In this process, which is conducted in the liquid phase, the molar ratio of γ-butyrolactone to monomethylamine in the reactor is between 1:1.08 and 1:1.2 at a temperature of from 320° C. to 380° C. and at a pressure of from 70 to 120 bar. It is suggested that the amount of water present in the reaction should not exceed 10 wt %. However, the high temperatures used in the process promote the formation of by-products and compounds which colour the finished N-methyl-pyrrolidone.

An alternative process is described in WO 99/52867. Here the process for the reaction of monomethylamine and γ-butyrolactone to N-methyl-pyrrolidone and water is carried out in three distinct reaction stages. The first stage of the reaction is carried out at a temperature of from about 150° C. to about 220° C. at the first stage reactor outlet and with a residence time ranging from 5 to 30 minutes. The second stage of the reaction is carried out at a temperature ranging from about 220° C. to about 270° C. at a second stage reactor inlet and a residence time ranging between 1 and 3 hours. The third stage of the reaction is carried out at a temperature ranging between 250° C. and 310° C. at the third stage reactor inlet and a residence time ranging between 0.5 and 2.0 hours. In the first step the monomethylamine and γ-butyrolactone combine to form 4-hydroxy-n-methylbutylamide. The second step is the reaction of 4-hydroxy-n-methylbutylamide to form N-methylamine. As this second step is relatively slow, high temperatures and long residence times are required for this part of the reaction. It is suggested that advantages may be observed where the molar ratio of monomethylamine to γ-butyrolactone is from about 1.05:1 to about 1.4:1.

JP 2001/002640A describes a process for the manufacture of N-methyl-pyrrolidone by reacting γ-butyrolactone and monomethylamine in the presence of water in which the reactor effluent is fed to a first distillation column where 2 to 15 wt % of the N-methyl-pyrrolidone in the feed is extracted from the column bottom. The water, monomethylamine and the remaining N-methyl-pyrrolidone are taken from the column top and supplied to a second distillation column where water and monomethylamine and water are removed from the top and the N-methyl-pyrrolidone is removed from the bottom of the column.

Alternative processes for producing N-methyl-pyrrolidone are described in JP2000/256312A, JP2001/354646A and JP2001/354647A.

The prior art shows that it is common practice to separate the N-methyl-pyrrolidone from the other components in the reactor stream by distillation. Unfortunately any γ-butyrolactone remaining in the product stream from the reactor is difficult to separate from the desired pyrrolidone and is therefore likely to remain as a contaminant in the product. It is therefore often necessary to use a dosing chemical such as sodium hydroxide to assist in the removal of γ-butyrolactone. For example, in U.S. Pat. No. 2,964,535 a procedure for the removal of γ-butyrolactone from the N-methyl-pyrrolidone product is described in which the reactor stream is treated with an alkali metal hydroxide solution prior to the distillation step.

The presence of contaminating γ-butyrolactone in the pyrrolidone product may be due not only to unreacted γ-butyrolactone from the feed but also to the formation of γ-butyrolactone in the distillation columns. This is due to the presence of unconverted intermediate 4-hydroxy-n-alkylbutylamide leaving the reactor in the product stream and reverting to γ-butyrolactone and monoalkylamine under the distillation conditions. This reversion reaction is promoted as the monoalkylamine, which is relatively volatile, is driven off during the distillation. This most commonly occurs where the temperature for distillation is relatively high, for example in the column sump. In particular, reversion of the 4-hydroxy-n-alkylbutylamide to the γ-butyrolactone will occur at temperatures greater than about 150° C. to 180° C.

Impurities in the product pyrrolidone may be due to the presence of impurities in the commercially available starting materials. Commercial γ-butyrolactone may be contaminated with tetrahydrofuran. Impurities in commercial monoalkylamine may include dialkylamine and trialkylamine. Thus where the amine used is monomethylamine, it may be contaminated with dimethylamine and trimethylamine. Tetrahydrofuran, dimethylamine and trimethylamine and other light boiling impurities can concentrate in the distillation column, particularly in a stream which comprises predominately monoalkylamine and water. Their presence will reduce the bubble point of the stream.

When taken together, the prior art teaches that it is advantageous to minimise the amount of water in the reactor feed, to operate at a small molar excess of monoalkylamine to γ-butyrolactone and to carry out the distillation to obtain the desired pyrrolidone at sub-atmospheric pressure. However, these processes leave the problem of how to produce high-purity pyrrolidone with good colour without having to carry out excessively expensive separation processes. For example, when the concentration of water in the feed to the reactor approaches zero and the molar ratio of monomethylamine to γ-butyrolactone is greater than about 1.05, it is not possible to condense the mixture of monoalkylamine, water and the low boiling impurities that are isolated in the distillation system at pressures below about 0.2 bara. Whilst refrigeration could be used to condense this stream, such a process would be expensive in terms of capital and operating costs.

A second alternative solution would be to consider compressing the overhead vapours so that they can be supplied to downstream units or condensed under increased pressure. However, this solution would also require high capital and operating costs.

In order to address these disadvantages and drawbacks it has now been found that if water is added to the distillation system it is possible to raise the dew point of the overheads mixture to a level where it can be condensed using cooling water. Whilst there is a small additional energy load and hence a corresponding cost implication associated with the addition of the water to the distillation system, this additional duty is outweighed by the saving of not having to use compression or refrigeration.

Thus according to the present invention there is provided a process for the production of N-alkylpyrrolidone from γ-butyrolactone and monoalkylamine in the liquid phase comprising the steps of:

feeding monoalkylamine and γ-butyrolactone, in the absence of water or in the presence of less than about 1 wt % of water, to a reaction zone to form a reaction mixture;

heating the reaction mixture;

withdrawing a product stream from the reaction zone and passing the stream to a distillation zone comprising at least one distillation column operated at sub-atmospheric pressure;

adding water to the distillation zone;

isolating at least one overhead stream from the distillation zone comprising monoalkylamine, water and optionally N-alkyl-pyrrolidone and condensing the overhead stream against cooling water.

The water added to the distillation zone may be added directly thereto or may be added to the product stream prior before it is fed to the distillation zone.

It will be acknowledged that the addition of water to a distillation zone to reduce the cost of separation is contrary to the established teachings.

A further benefit is that adding water to the distillation zone allows cooling water to be used as the condensing medium which offers substantial cost advantages.

The monoalkylamine, γ-butyrolactone and any water may be pre-mixed before being added to the reaction zone.

The reaction will generally be carried out at a molar excess of monoalkylamine. Whilst there is an advantage to operating at lower molar excesses, the advantage diminishes as the molar ratio approaches 1.05:1 and thus the molar excess used in the process of the present invention will generally be at least 1.05:1, monoalkylamine:γ-butyrolactone. Not wishing to be bound by any theory, it is believed that unreacted γ-butyrolactone can pass through the reactor due to equilibrium restrictions. Further, if only a very small molar excess of monoalkylamine over γ-butyrolactone is present, a small control upset of the feed flow of monoalkylamine or γ-butyrolactone could cause a large slippage of γ-butyrolactone out of the reactor which will be difficult to separate from the pyrrolidone product.

Where water is present, the amount of water present in the reaction mixture is less than 1 wt %. Any water present may be from the γ-butyrolactone feed, from the monoalkylamine feed or from both feeds. Water may also be present in any recycle stream. However, it is preferred that any water present is reduced as much as possible. Thus amounts of less than 0.2 wt % may be utilised. Whilst the reaction can be carried out in the absence of water, the rate of reaction obtained in the absence of water may be unacceptably low.

The reaction will generally be conducted in the absence of additional catalyst.

The distillation zone preferably comprises more than one distillation column. For example, two or three distillation columns may be used. Where more than one distillation column is used they may each be operated at sub-atmospheric pressure. Any suitable pressure may be used. However, pressures of from about 0.05 bara and about 0.3 bara are particularly suitable. Operating the distillation at the sub-atmospheric pressure enables lower temperatures to be used and thereby minimises the possibility of the reversion reaction of intermediate 4-hydroxy-n-alkylbutylamide to γ-butyrolactone. Thus, the presence of γ-butyrolactone as a contaminant in the product pyrrolidone is minimised.

The water supplied to the distillation zone may be from any suitable source. For example, it may be distilled water. The water may be supplied by any suitable method but is preferably supplied directly to the distillation zone. In one arrangement, the water may be supplied to an overhead condenser or it may be supplied between the distillation column and the overhead condenser or any suitable point may be selected to add water to the distillation zone. The water will generally be supplied to the top of the distillation column. The amount of water added to the distillation zone will depend on the pressure of the at least one distillation column, the temperature of the available cooling water and the molar excess of monoalkylamine used.

Any suitable temperature and residence times may be used for the or each distillation columns. Where there is more than one distillation column present. The temperatures, pressures and residence time may be the same or different.

Where more than one stream is isolated from the distillation zone comprising monoalkylamine, water and optionally some N-alkylpyrrolidone they may be condensed against cooling water separately. However, more usually they will be combined before being condensed against the cooling water.

The cooling water used may be made of any suitable temperature. Temperatures of from about 5° C. to about 35° C. may be used. The condensing of the overhead stream will generally take place in a heat exchanger.

The flow rate of the cooling water may be adjusted to provide process-side condensing temperature goals. This goal may be set at any suitable level above the maximum temperature of the cooling medium. For example, the goal could be selected to be from about 1 to about 30° C. above the maximum temperature of the cooling water. This will have the benefit of minimising the amount of water that has to be added to the distillation as the temperature of the available cooling water changes. For example, in temperate climates in winter when the cooling water is much colder than in the summer, the amount of water added to the at least one distillation column can be reduced.

The monoalkylamine utilised will preferably comprise less than 0.5 wt % and more preferably less than 0.1 wt % total dimethylamine and trimethylamine alkylamine content.

The process of the present invention will generally provide almost complete conversion of monoalkylamine and γ-butyrolactone such that the concentration of γ-butyrolactone leaving the reactor is generally less than 500 ppm and may be less than 100 ppm. It will also generally provide conversion of the intermediate amide at the exit from the reactor of above 98%.

Any suitable kind of reactor and distillation apparatus may be used. In one arrangement, the reactor may be a piston-type reactor that has flow through separate compartments to prevent remixing of products.

The monoalkylamine is preferably monomethylamine such that the product obtained is N-methyl-pyrrolidone.

The present invention will now be described by way of example with reference to FIG. 1 which is a schematic diagram of one embodiment of the present invention.

γ-butyrolactone is fed in line 1 and then mixed with monoalkylamine, such as monomethylamine, which is fed in line 2. It will also be mixed with recycled monoalkylamine fed in line 3 from downstream. The mixture is fed in line 4 to a reaction zone 5 and heated to the required reaction temperature. The temperature is maintained at the required level by heat exchange. A stream 6 of reactor effluent, which substantially comprises N-alkylpyrrolidone, water, monoalkylamine, and a small quantity of 4-hydroxy-n-alkylbutylamide and heavy by-products, is fed to the distillation zone which comprises a first distillation column 8, a second distillation column 9 and a third distillation zone 10 through which at least some of the reactor effluent passes sequentially. It will be understood that some of the reactor effluent may be withdrawn prior to the distillation zone, some may be removed after the first distillation column, and/or some may be removed after the second distillation column.

Water is added in line 11 The first distillation column 8 is operated at sub-atmospheric pressure. A stream of N-alkylpyrrolidone, 4-hydroxy-n-alkylbutylamide and heavy by-products is removed from the bottom of column 8 in line 12. A stream 13 comprising N-alkyl-pyrrolidone, water and monomethylamine is removed from the top of the first distillation column 8 and fed to the second distillation column 9 which is operated at sub-atmospheric pressure. Water is added to this column 9 in line 14. A stream of N-alkyl-pyrrolidone is removed from the bottom of column 9 in line 15. A stream 16 comprising water and monoalkylamine is removed from the top of the second distillation column 9 and fed to the third distillation column 10 where the monoalkylamine is separated overhead and recycled in line 3. The water is removed in line 17.

The quantity of water added to the first distillation column 8 in line 11 is controlled so that stream 6 can be condensed at the pressure of distillation column 8 using available cooling water. Similarly the quantity of water added in line 14 to the second distillation column 9 is controlled so that stream 13 can be condensed at the pressure of the second distillation column 9 using available cooling water.

Whilst the process has been described with reference to adding water to the first and second distillation columns, it will be understood that benefits can be achieved by adding water to the first, second or the first and second distillation column.

The benefits of the present invention will now be described with reference to the following examples for the production of N-methyl-pyrrolidone from γ-butyrolactone and monomethylamine.

EXAMPLE 1 AND COMPARATIVE EXAMPLE 1

Example 1 relates to a process for the production N-methyl-pyrrolidone in accordance with the present invention in the absence of water in the reactor and the addition of water to the second distillation column and Comparative Example 1 corresponds to the process described in JP2001/002640A. Table 1 sets out the water needed in a mixture of monomethylamine and water to achieve a bubble point of 40° C. or greater.

TABLE 1

|  | Example 1 | Comparative Example 1 |
|---|---|---|
| Molar ratio of γ-butyrolactone:monomethylamine:water in reactor feed | 1:1.1:0 | 1:1.1:2.9 |
| Molar ratio of monomethylamine:water in the feed to the third distillation column if no water is added to the distillation area. | 0.1:1.0 | 0.1:3.9 |
| Approximate bubblepoint @ 0.2 bara (° C.) of the feed to the third distillation column if no water is added to the distillation area. | 38 | 52 |
| Water that must be added to the distillation to elevate the bubble point to 40° C. or greater | 0.15 moles per mole of γ-butyrolactone fed to the reactor | no water added |
| Total water that must be removed from the distillation when process side can be condensed at 40° C. or greater | 1.15 moles per mole of γ-butyrolactone fed to the reactor | 3.9 moles per mole of γ-butyrolactone fed to the reactor |

During hot summer conditions the cooling water temperature can be taken hypothetically as 40° C. Where the minimum temperature approach for the condenser on the second distillation column (9) is 10° C., the process side bubble point must be 50° C. to condense the overheads from the second distillation column. It is necessary to add about 2.3 moles of water per mole of γ-butyrolactone fed to the reactor to the second distillation column to elevate the bubble point of the monomethylamine and water mixture to 50° C. Hence there is an advantage over the comparative example during hot summer months.

However, during winter the noted advantage can be much larger. If the cooling water is at a temperature of 30° C. the bubble point requirement is 40° C. if a 10° C. cooler approach temperature is assumed. The flow of water to the second distillation column can now be controlled to just 0.15 moles per mole of γ-butyrolactone fed to the reactor. Thus as detailed in Table 1 above there is a large advantage over the comparative examples.

In addition to the noted advantage of having to remove less water from the distillation zone the reactor volume can be utilised more effectively since there is less water present.

The N-methyl-pyrrolidone produced in accordance with the present invention can be produced in a cost-effective manner. In addition, it will have good colour due to the absence of impurities.

The invention claimed is:

1. A process for the production of N-alkyl-pyrrolidone from γ-butyrolactone and monoalkylamine in the liquid phase comprising the steps of:
    feeding monoalkylamine and γ-butyrolactone, in the absence of water or in the presence of less than about 1 wt % of water, to a reaction zone to form a reaction mixture;
    heating the reaction mixture;
    withdrawing a product stream from the reaction zone and passing the stream to a distillation zone comprising at least one distillation column operated at sub-atmospheric pressure;
    adding water to the distillation zone;
    isolating at least one overhead stream from the distillation zone comprising monoalkylamine, water and optionally N-alkyl-pyrrolidone and condensing the overhead stream against cooling water.

2. A process according to claim 1 wherein the reaction mixture comprises a molar excess of monoalkylamine to γ-butyrolactone.

3. A process according to claim 2 where the molar excess is at least 1.05:1.

4. A process according to claim 1 wherein the water present in the reaction mixture is less than 0.2 wt %.

5. A process according to claim 1 wherein two or three distillation columns are used.

6. A process according to claim 5 wherein each distillation column is operated at sub-atmospheric pressure.

7. A process according to claim 1 wherein the pressure of the at least one distillation column is from about 0.05 bar absolute to about 0.3 bar absolute.

8. A process according to claim 1 wherein the water added to the distillation zone is added directly to the at least one distillation column operated at sub-atmospheric pressure.

9. A process according to claim 1 wherein the temperature of the cooling water is from about 5° C. to about 35° C.

10. A process according to claim 1 wherein the monoalkylamine is monomethylamine and the product is N-methyl-pyrrolidone.

* * * * *